US011389429B2

United States Patent
Shin et al.

(10) Patent No.: US 11,389,429 B2
(45) Date of Patent: Jul. 19, 2022

(54) USE OF CARBAMATE COMPOUND FOR PREVENTING, ALLEVIATING OR TREATING MYOTONIA

(71) Applicant: SK BIOPHARMACEUTICALS CO., LTD., Gyeonggi-do (KR)

(72) Inventors: Hye Won Shin, Gyeonggi-do (KR); Ji Hye Kim, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 125 days.

(21) Appl. No.: 16/763,718

(22) PCT Filed: Nov. 13, 2018

(86) PCT No.: PCT/KR2018/013767
§ 371 (c)(1),
(2) Date: May 13, 2020

(87) PCT Pub. No.: WO2019/098632
PCT Pub. Date: May 23, 2019

(65) Prior Publication Data
US 2021/0401804 A1     Dec. 30, 2021

(30) Foreign Application Priority Data
Nov. 14, 2017   (KR) .................. 10-2017-0151241

(51) Int. Cl.
*A61K 31/41*   (2006.01)
*A61P 21/00*   (2006.01)
*A61K 9/00*    (2006.01)

(52) U.S. Cl.
CPC ............ *A61K 31/41* (2013.01); *A61K 9/0019* (2013.01); *A61P 21/00* (2018.01)

(58) Field of Classification Search
CPC .................. A61K 31/41; A61P 21/00
See application file for complete search history.

(56) References Cited

U.S. PATENT DOCUMENTS

| 2012/0004211 A1 | 1/2012 | Jagerovic et al. |
| 2017/0029382 A1 | 2/2017 | Bosmans et al. |

FOREIGN PATENT DOCUMENTS

| KR | 10-1286499 B1 | 7/2013 |
| WO | WO-2006-048771 A1 | 5/2006 |
| WO | WO-2006-112685 A1 | 10/2006 |
| WO | WO-2010-150946 A1 | 12/2010 |
| WO | WO-2011-046380 A2 | 4/2011 |
| WO | WO-2017-097311 A1 | 6/2017 |

OTHER PUBLICATIONS

Bialer, et al. (2015) Progress report on new antiepileptic drugs: A summary of the Twelfth Eilat Conference (EILAT XII). *Epilepsy Research*, 111:85-141.
Turner. C. et al. (2010) "The Myotonic Dystrophies: Diagnosis and Management.", *Journal of Neurology, Neurosurgery and Psychiatry*, 81:358-367.
International Search Report issued in International Patent Application No. PCT/KR2018/013767, dated Feb. 13, 2019, with English Translation.
Desaphy, et al. (2013) "In vivo evaluation of antimyotonic efficacy of β-adrenergic drugs in a rat model of myotonia." *Neuropharmacology* 65:21-27.
De Bellis, et al. (2017) "Increased sodium channel use-dependent inhibition by a new potent analogue of tocainide greatly enhances in vivo antimyotonic activity." *Neuropharmacology*, 113:206-216.
Extended European Search Report from corresponding European Patent Application No. 18877792.4, dated Oct. 20, 2021.
Golyala, A., et al.; "Drug development for refractory epilepsy: The past 25 years and beyond", Seizure, 44 (2017) 147-156.

*Primary Examiner* — Kamal A Saeed
(74) *Attorney, Agent, or Firm* — Harness, Dickey & Pierce, P.L.C.

(57) ABSTRACT

The present invention relates to a use of a carbamate compound represented by chemical formula 1, or a pharmaceutically acceptable salt, a solvate or a hydrate thereof for preventing, alleviating or treating myotonia.

8 Claims, 3 Drawing Sheets

*: The disease model test compound 20mg/kg has statistical significance in comparison with the untreated group (P <0.05)

*: The disease model test compound 20mg/kg has statistical significance in comparison with the untreated group (P <0.05)

USE OF CARBAMATE COMPOUND FOR PREVENTING, ALLEVIATING OR TREATING MYOTONIA

CROSS-REFERENCE TO RELATED APPLICATIONS

This application is a national phase application of PCT Application No. PCT/KR2018/013767, filed on Nov. 13, 2018, which claims priority to Korean Patent Application No. 10-2017-0151241, filed on Nov. 14, 2017. The entire disclosure of the applications identified in this paragraph is incorporated herein by reference.

FIELD

The present invention relates to use of carbamate compounds of the following Formula 1, or a pharmaceutically acceptable salt, solvate or hydrate thereof for the purpose of preventing, alleviating or treating myotonia.

[Formula 1]

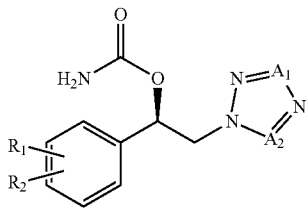

wherein, $R_1$, $R_2$, $A_1$ and $A_2$ are as defined herein.

BACKGROUND

Myotonia refers to a condition in which muscles do not relax after contraction and appears in autosomal dominant diseases such as myotonic dystrophy, myotonia congenita and paramyotonia congenita.

Myotonic dystrophy is a disease that occurs in five out of about 100,000 people, and most frequently appears in hereditary myotonia in adults. Myotonic dystrophy is also referred to as dystopy myotonica or Steinert's disease, and shows a condition which progresses to myoatrophy or muscle weakness after showing symptoms of spasticity. It is caused by the triplet repeat on the chromosome 19 long arm. Muscular atrophy appears mainly on the distal muscle, and shows a disorder in the extensor of the upper limb or symptoms of facial muscle atrophy. Myotonic dystrophy includes two major types, DM type 1 and DM type 2, and it affects the normal expression of chloride channel-1 (CLCN1). Abnormal chloride flow in the skeletal muscle cells and insufficient concentration of chloride in cells cause myotonia.

Myotonia congenita is a rare disease that is inherited as autosomal dominant or recessive. It shows a characteristic that takes time to relax the muscles by increasing spasticity of voluntary muscles when exercising. Muscular hypertrophy may also occur with an increase in spasticity, and if abnormal symptoms by muscle relaxation are expanded into the facial, ocular and tongue muscles, it may cause speech disorders. Myotonia congenita include two types: Becker's disease and Thomsen's disease. Both diseases are caused by mutations in CLCN1 gene expressing chloride channel-1, and occur a variety of phenotypes with more than 130 various mutations. Abnormalities of chloride channel-1 can lead to myotonia as described in said myotonic dystrophy. Myotonia which appears in myotonia congenita occurs more often in pregnant women.

Paramyotonia congenita is caused by mutations in SCN4 gene expressing the voltage-gated sodium channel 1.4. These mutations generate spontaneous action potential after voluntary movement by preventing the normal channel inactivation. Myotonic symptoms mainly appears in the face and limbs. In addition to myotonic symptoms, a cycle of limb muscle paralysis occurs when serum potassium rises.

Myoatrophy which appears in myotonia is caused by hyperexcitability of the sarcolemma and causes pain and mobility difficulty in daily life. The hyperexcitability of the sarcolemma occurs due to the excessive action potential of the muscle cell. Mexiletine, which is also used as a treatment for ventricular arrhythmia, is currently in clinical trials for patients with myotonia, and induces muscle relaxation by blocking the 1,4-type voltage-gated sodium channel of skeletal muscles, thereby inhibiting the action potential release during myoatrophy. Mexiletine also alleviates the muscle weakness of myotonia congenita caused by chloride channel-1 mutation (CLCN1 mutation). However, mexiletine is difficult to apply as a therapeutic agent for myotonia due to side effects and lack of drug efficacy. Tocanide, which is oral lidocaine analogue, has also been used to treat myotonia, but sales have been discontinued in many countries due to serious side effects (M. De Bellis et al., 2017, Neuropharmacology, 113: 206-216).

To date, drugs for the treatment of myotonia are being developed in the absence of appropriate therapeutic agents.

SUMMARY

Problem to be Solved

The present invention is intended to provide a method for the prevention, alleviation or treatment of myotonia.

In addition, the present invention is intended to provide the use of a carbamate compound of the following Formula 1, or a pharmaceutically acceptable salt, solvate or hydrate thereof for the prevention, alleviation or treatment of myotonia:

[Formula 1]

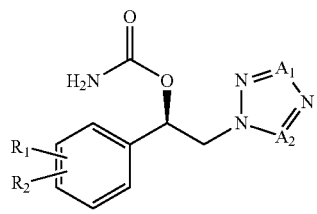

wherein, $R_1$, $R_2$, $A_1$ and $A_2$ are as defined herein.

Technical Solution to the Problem

The present invention provides a medicament for the prevention, alleviation or treatment of myotonia, comprising a therapeutically effective amount of a carbamate compound of the following Formula 1, or a pharmaceutically acceptable salt, solvate or hydrate thereof:

[Formula 1]

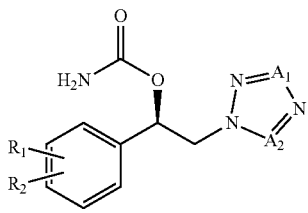

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention, alleviation or treatment of myotonia, comprising a therapeutically effective amount of the carbamate compounds of the above Formula 1, or a pharmaceutically acceptable salt, solvate or hydrate thereof, and further one or more of a pharmaceutically acceptable carrier.

In addition, the present invention provides a method for preventing, alleviating or treating myotonia, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention, alleviation or treatment of myotonia.

According to one embodiment of the present invention, in the above Formula 1, $R_1$ and $R_2$ are each independently selected from the group consisting of hydrogen, halogen and $C_1$-$C_8$ alkyl.

In one embodiment, halo-$C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

[Formula 2]

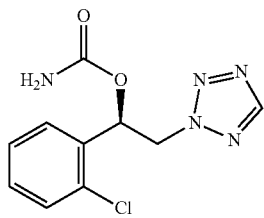

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in International Publication Nos. WO 2006/112685 A1, WO 2010/150946 A1 and WO 2011/046380 A2, the disclosures of which are incorporated herein by reference. The compounds of Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula I can be used for the prevention, alleviation or treatment of myotonia.

According to one embodiment of the present invention, the disease which represents myotonia may be one or more selected from myotonia congenita comprising myotonic dystrophy (Steinert's disease); Becker's disease and Thomsen's disease; and paramyotonia congenita. The myotonic dystrophy may be type 1 or type 2.

According to one embodiment, myotonia may be a sporadic etiology or a hereditary etiology involving a family history. In addition, myotonia may be caused by abnormality of the gene (CLCN1) expressing chloride channel-1 or the gene (SCN4) expressing the voltage-gated sodium channel 1.4. In addition, sustained excitability maintenance of muscle cells by hyperexcitability of muscle cells in this disease is one of the main mechanisms (Kwiecinski et al., 1984, Muscle & Nerve, 7(1): 60-5; Lossin et al., 2008, Advances in Genetics, 63: 25-55). Myotonia related to CLCN1 gene mutations includes Thomsen's disease, Becker's disease, myotonia congenita, generalized myotonia, myotonia levior. Diseases related to SCN4A gene mutations include paramyotonia congenita, potassium aggravated myotonia, myotonic fluctuans, myotonia permanens or acetazolamide responsive myotonia.

Symptoms of myotonic dystrophy begin with muscle weakness in the hands, feet, neck or face, and the muscle weakness gradually progresses to other muscles including the heart. Problems of executive function and symptoms of hypersomnia may occur.

Adult-onset myotonic dystrophy type 1 can cause cataracts, myotonia and diabetes. In serious cases, muscle weakness may occur in specific muscles (upper eyelid levators, masticator muscles, neck muscles, specific limb muscles, etc.). Muscle pain and fatigue are common symptoms. Initiation of adolescent myotonic dystrophy type 1 may have symptoms of muscle weakness or spasticity. They may have difficulty with a learning deficiency or a social behavior and may have disorders with speech or hearing. They may have heart-related symptoms such as arrhythmia, which may not be accompanied by other symptoms. Adolescent myotonic dystrophy type 2 has weaker symptoms than type 1. From birth, congenital myotonic dystrophy type 1 is the most serious type of myotonic dystrophy. It shows serious muscle weakness and muscular hypotonia symptoms at birth. Some infants show deteriorating eyesight, hyperopia and astigmatism. Intellectual disabilities can occur, and learning and behavioral disorder can continue to develop as they grow. In addition, growth deficiency due to dietary disorders may occur, and gastroparesis can cause persistent digestive symptoms such as nausea. Congenital myotonic dystrophy disease can cause respiratory problems due to muscle weakness. This is a major cause of death of the disease. Congenital myotonic dystrophy disease develops as adult-onset myotonic dystrophy and causes heart-related problems. Myotonic dystrophy type 2 shows muscle weakness, muscle pain, spasticity or cataract, and some patients do not have these symptoms. The degree of symptoms and the types of symptoms appear differently for each individual patient. Cardiac function abnormalities appear less frequently than in type 1, but can rarely cause death.

Myotonia congenita is a disease of the voluntary muscles (skeletal muscles) abnormality that responds to hyperexcitability of the specific muscular fibers and causes cramps, abnormal muscle stiffness and spasticity. Symptoms tend to occur when a patient uses specific muscles after a refractory period. Myotonia congenita patients mostly develop abnormal hypertrophy of the voluntary muscles.

Paramyotonia congenita is a rare non-progressive genetic disorder that affects skeletal muscles. The main symptoms are muscle stiffness and spasticity, which are mainly shown in the muscles of the face, neck and upper limbs, and may also occur in muscles related to breathing or deglutition movement or back muscles. It shows no muscular atrophy, and partly appears as muscle hypertrophy. The severity of muscle stiffness varies from person to person, and some patients are accompanied by pain with spasticity.

The carbamate compounds of the above Formula 1 may be applied to myotonia by suppressing the excitability maintenance of neuron cells. In addition, the carbamate compounds of the above Formula 1 may be used to prevent, alleviate or treat various symptoms related to myotonia—for example, muscle stiffness, spasticity, distal muscle weakness, weakness of the face and jaw muscles, difficulty in swallowing, sagging of the eyelids (blepharosis), weakness of the neck muscles, weakness of the arm and leg muscles, persistent muscle pain, excessive sleep, muscle wasting, dysphagia, respiratory failure, irregular heartbeat, heart muscle damage etc.

The efficacy for myotonia of the compounds of the above Formula 1 can be confirmed by the use of known models. For example, the efficacy of the compounds of the above Formula 1 may be evaluated in a myotonia model caused by anthracene-9-carboxylic acid (9-AC). Anthracene-9-carboxylic acid can cause myotonic conditions by blocking the chloride channel-1 of muscle cells. Myotonic conditions are induced by intraperitoneal injection once to experimental animals (rats), and can be evaluated by measuring the righting reflex time. Righting reflex is a reflex behavior in which the animal's body returns from an abnormal position to a normal position, and the degree of myotonia can be evaluated by measurement of righting reflex behavior due to abnormality of muscle tension/relaxation after 9-AC treatment. Specifically, the degree of spasticity is evaluated by measuring the time that it takes for the four feet of the experimental animal to land normally when the experimental animal is turned upside down and the posture is straightened (time of righting reflex, TRR).

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect—i.e., the therapeutic effect as described above. The therapeutically effective amount of the compounds of Formula 1 is 50 to 500 mg, 50 to 400 mg, 50 to 300 mg, 100 to 400 mg, 100 to 300 mg, 50 to 200 mg or 100 to 200 mg, based on the free form and once-daily administration to humans.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise compounds selected from the group consisting of the carbamate compounds of a therapeutically effective amount of the present invention, their pharmaceutically acceptable salts, solvates, hydrates and combinations thereof.

Examples of the pharmaceutically acceptable salts of the carbamate compounds of the above Formula 1 include independently, for example, acetate, benzenesulfonate, benzoate, bitartrate, calcium acetate, camsylate, carbonate, citrate, edetate, edisylate, estolate, esylate, fumarate, gluceptate, gluconate, glutamate, glycoloylarsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment may be formulated as a plain tablet (uncoated tablet) or such that the active agent is coated or is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, preferably 50 to 300 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat and prevent myotonia. The medicament and the pharmaceutical composition can not only relieve the burst of muscle cell action potential, but also suppress the onset of the burst.

DETAILED DESCRIPTION

Hereinafter, the present invention will be explained in more detail thorough working examples. However, the following working examples are only intended to illustrate one or more embodiments and are not intended to limit the scope of the invention.

Preparation Example: Preparation of carbamic acid (R)-1-(2-chlorophenyl)-2-tetrazol-2-yl-ethyl ester Carbamic acid (R)-1-(2-chlorophenyl)-2-tetrazol-2-yl-ethyl ester (test compound) was prepared according to the method described in Preparation Example 50 of International Publication No. WO 2010/150946.

Example: Experiment Using Myotonia Induction Model by Drug (9-AC) Treatment

In the experimental animal model of myotonia induction by drug (9-AC) treatment, it was reported that the time to return to normal posture after righting reflex was delayed when measuring the rat's spasticity conditions using righting reflex (Desaphy et al., 2013, Neuropharmacology, 65: 21-27).

As an experimental model, Sprague-Dawley rats (350-400 g, 10 weeks old, a total of 36 males) were used (Orient Bio Inc.). The drug anthracene-9-carboxylic acid (9-AC)

used to induce myotonia is a drug that inhibits chloride channel-1 of skeletal muscle cells and induces hyperexcitation of muscle cells. The control group (30% PEG300) or test compound was intraperitoneally administered to the rat once in each dose (15, 20 mg/kg). Test compounds were diluted in 30% PEG300 solution to a final dose of 5 ml/kg. After 20 minutes of administration of control group or test compound, 0.3% NaHCO$_3$ solution containing 6 mg/ml of 9-AC was intraperitoneally administered by 10 ml/kg. After administration of 9-AC, righting reflex tests were performed at 30 minutes and 1 hour, respectively, and the time to return to normal posture (time of righting reflex, TRR) was measured.

Figure 1:
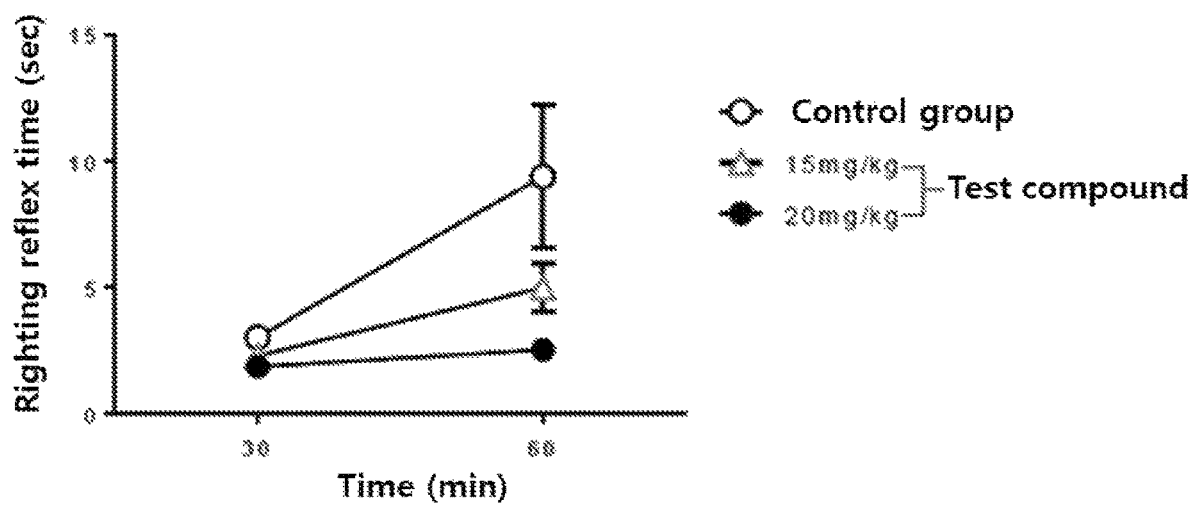
FIG. 1 is a result through righting reflex test to confirm whether the spasticity conditions are alleviated, and the spasticity conditions are induced when 15 mg/kg and 20 mg/kg of carbamic acid (R)-1-(2-chlorophenyl)-2-tetrazol-2-yl-ethyl ester (hereinafter referred to as "test compound") prepared in the Preparation Example was injected intraperitoneally into rats, respectively, and then after 20 minutes, anthracene-9-carboxylic acid (9-AC) was injected intraperitoneally. Righting reflex was measured after 30 minutes and 1 hour, respectively, after administration of 9-AC. The control group was administered only 30% PEG 300 without the addition of the test compound.
Figure 2:
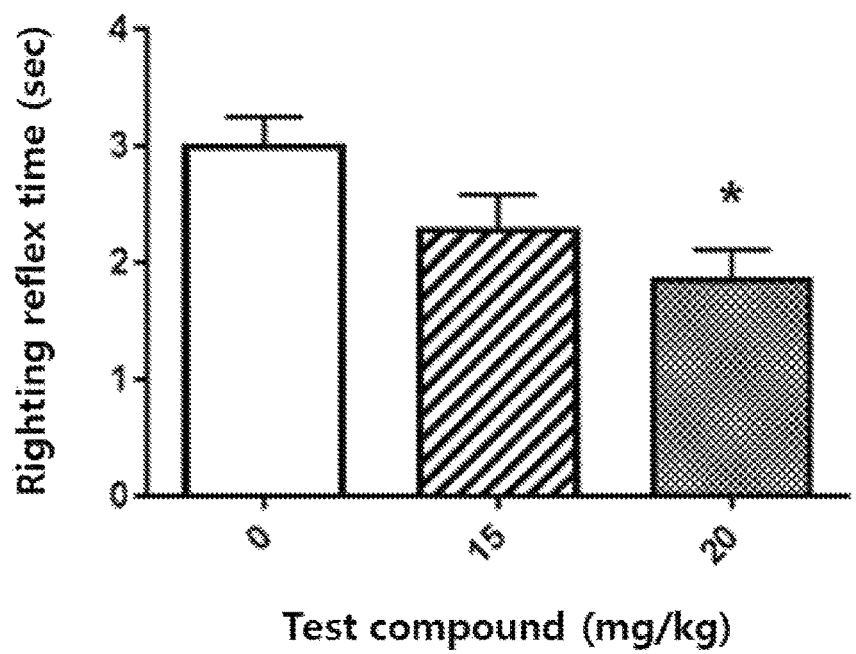
FIG. 2 is a result of comparing and confirming the righting reflex time with the control group: the righting reflex time was measured when 15 mg/kg or 20 mg/kg of the test compound was respectively administered, and then after 20 minutes, 9-AC was administered, and after 30 minutes.
Figure 3:
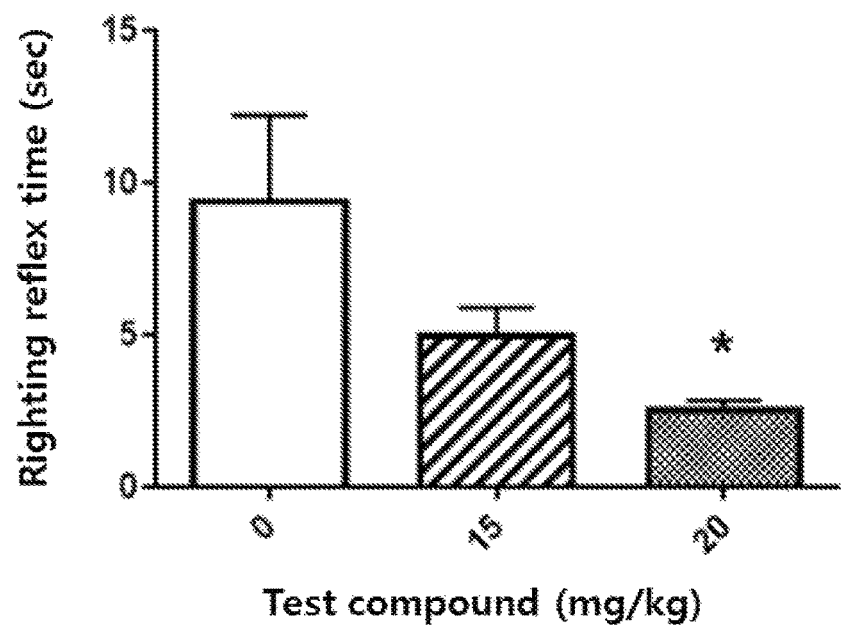
FIG. 3 is a result of comparing and confirming the righting reflex time with the control group: the righting reflex time was measured when 15 mg/kg or 20 mg/kg of the test compound was respectively administered, and then after 20 minutes, 9-AC was administered, and after 1 hour.

When 30 minutes and 1 hour had elapsed after the spasticity was induced, the test compound showed results of a decrease in time to return to normal posture compared to the control group in righting reflex test. Over time, the control group showed results of an increase in the time to return to the normal posture in the righting reflex test, but in the group treated with the test compound, this tendency was alleviated (FIG. 1). These results demonstrate that the test compound can alleviate myotonia. Differential time reduction results were shown depending on the dose of the test compound, and at both 30 minutes and 1 hour, the 20 mg/kg dose of the test compound showed a significant time reduction effect compared to the control group (P<0.05) (FIG. 2, FIG. 3). Statistical analysis was used for the one-way ANOVA (1-way ANOVA) and Tukey's multiple comparison test, and outliers were excluded through the ROUT outlier analysis test (Q=1%) (in the 30-minute test, excluding each one in the control group and the 20 mg/kg treatment group; in the 1-hour test, excluding one in the 20 mg/kg treatment group). The results were derived from three repeated experiments. The average value of the righting reflex time measured for each group is shown in Table 1 below.

TABLE 1

| Average Righting reflex time (TRR) | Control group | Test compound 15 mg/kg | Test compound 20 mg/kg |
| --- | --- | --- | --- |
| 30 minutes | 3 ± 0.254 (n = 8) | 2.282 ± 0.304 (n = 9) | 1.85 ± 0.266 (n = 8) |
| 1 hour | 9.397 ± 2.834 (n = 9) | 4.978 ± 0.944 (n = 9) | 2.515 ± 0.328 (n = 8) |

From the above results, by showing the efficacy of alleviating spasticity which appears in myotonia, it was confirmed that the compound of Formula 1 (test compound) can be used as a drug for the prevention and treatment of myotonia.

What is claimed is:

1. A method for alleviating or treating myotonia, comprising administering to a subject in need thereof a therapeutically effective amount of a carbamate compound which is carbamic acid (R)-1-(2-chlorophenyl)-2-tetrazol-2-yl) ethyl ester of the following Formula 2, or a pharmaceutically acceptable salt, solvate or hydrate thereof:

[Formula 2]

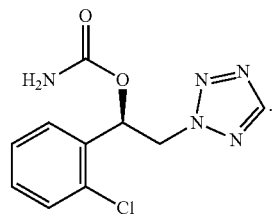

2. The method according to claim 1, wherein a disease which represents myotonia is at least one selected from myotonic dystrophy, myotonia congenita and paramyotonia congenita.

3. The method according to claim 1, wherein myotonia has a sporadic etiology.

4. The method according to claim 1, wherein myotonia has a hereditary etiology with a family history.

5. The method according to claim 2, wherein myotonic dystrophy is DM type 1 or DM type 2.

6. The method according to claim 2, wherein myotonia congenita is Becker's disease or Thomsen's disease.

7. The method according to claim 1, wherein the subject to be administered is a mammal.

8. The method according to claim 1, wherein the therapeutically effective amount of the carbamate compound of Formula 2 is 50 to 500 mg based on the free form when administered once a day.

* * * * *